(12) United States Patent
Han et al.

(10) Patent No.: US 7,517,690 B2
(45) Date of Patent: Apr. 14, 2009

(54) CELL LYSIS METHOD USING FREE RADICAL

(75) Inventors: Jung-im Han, Seoul (KR); Young-sun Lee, Gyeonggi-do (KR); Kak Namkoong, Seoul (KR); Kwang-wook Oh, Gyeonggi-do (KR)

(73) Assignee: Samsung Electronics Co., Ltd. (KR)

( * ) Notice: Subject to any disclaimer, the term of this patent is extended or adjusted under 35 U.S.C. 154(b) by 218 days.

(21) Appl. No.: 11/291,053

(22) Filed: Nov. 30, 2005

(65) Prior Publication Data

US 2006/0115902 A1 Jun. 1, 2006

(30) Foreign Application Priority Data

Nov. 30, 2004 (KR) .................. 10-2004-0099030

(51) Int. Cl.
*G01N 33/48* (2006.01)

(52) U.S. Cl. .................. 436/63; 436/73; 436/80; 436/83; 436/84; 436/135; 436/17; 436/174; 436/180; 436/149; 435/4; 435/5; 435/29

(58) Field of Classification Search .................. 436/63, 436/73, 80, 83, 84, 135, 17, 174, 177, 180, 436/149; 422/98, 99, 100, 101; 435/4, 5, 435/29

See application file for complete search history.

(56) References Cited

U.S. PATENT DOCUMENTS

| 4,740,282 | A | * | 4/1988 | Gesser et al. | ............... 204/165 |
| 5,135,850 | A | | 8/1992 | Prost | ............................ 435/29 |
| 6,524,456 | B1 | * | 2/2003 | Ramsey et al. | ............... 204/450 |
| 6,764,693 | B1 | | 7/2004 | Smith | ........................ 424/450 |

OTHER PUBLICATIONS

Taylor, Michael T. et al., "Lysing Bacterial Spores by Sonication through a Flexible Interface in a Microfluidic System," *Anal. Chem.* (2001) 73: 492-496.

* cited by examiner

*Primary Examiner*—Maureen M Wallenhorst
(74) *Attorney, Agent, or Firm*—Cantor Colburn LLP

(57) ABSTRACT

Provided is a method of lysing a cell or a virus using a free radical. The method includes: applying an electric field to a mixture of a metal ion, a peroxide, and a cell or virus solution to increase the free radical generation, thereby lysing a cell or a virus. In the present method, cell lysis may be efficiently performed using a low electrical energy (several mV to several V). When the present method is applied to a microsystem, cell lysis can occur at a desired time and in a desired space by controlling the electrical energy, thus being suitable to realize a lab-on-a-chip (LOC).

13 Claims, 4 Drawing Sheets

1.CONVENTIONAL METHOD

Fe (II) + $H_2O_2$

Fe(II)(aq) + $H_2O_2$(l) → Fe (III)(s) + $OH^-$(aq) + · OH

2. PHOTOCATALYTIC METHOD

UV-C LAMP (365nm)

Fe (III) + $H_2O_2$

Fe (III)
Fe (II)

3.ELECTROCHEMICAL CATALYTIC METHOD

Fe (III) + $H_2O_2$

CELL LYSIS METHOD USING FREE RADICAL

BACKGROUND OF THE INVENTION

This application claims the benefit of Korean Patent Application No. 10-2004-0099030, filed on Nov. 30, 2004, in the Korean Intellectual Property Office, the disclosure of which is incorporated herein in its entirety by reference.

1. Field of the Invention

The present invention relates to a method of lysing a cell using a free radical.

2. Description of the Related Art

In general, free radicals have adverse effects on organisms, particularly on their cells. Free radicals attack a cell wall at a rate depending on the cellular resistance provided by an enzymatic or a molecular mechanism of the cell. When the cell wall is decomposed by free radicals, holes are generated and contents of the cell flow out.

Cell lysis is typically performed using a mechanical, chemical, thermal, electrical, ultrasonic, or microwave method (Michael T. Taylor, et al., *Anal.Chem.*, 73, 492-496 (2001)).

A chemical method includes using a lysing agent to destroy a cell and release DNA from the cell. An additional process of treating the cell extract using a chaotropic reagent is required to denature the proteins. In this method, rough chemicals are used to destroy the cell. Since there is a probability that they can inhibit a subsequent polymerase chain reaction (PCR), DNA must be purified prior to performing the PCR. This method is labor-intensive, time-consuming, requires expensive supplies, and quite frequent, a recovery yield of DNA is low.

An electrical method uses dielectrophoresis. When a non-uniform electric field is applied to a neutral particle, such as a microorganism cell, the neutral particle is polarized and due to the non-unifomity of the electric field, a force is applied to the particle. The force induces a movement of the suspended cell, thus lysing the cell. However, cell lysis efficiency is low and high electrical power is required, and thus, this method is not suitable for a lab-on-a-chip (LOC).

U.S. Pat. No. 6,764,693 describes a composition which can inhibit generation of free radicals and a method of increasing intracellular and extracellular antioxidant effects. The patent describes an antioxidant which inhibits the actions of the free radicals, but it does not describe a cell lysis method using free radicals.

U.S. Pat. No. 5,135,850 describes a method of assaying or evaluating antioxidant activities of a living organism using free radicals. The patent describes cell lysis using free radicals, but it does not describe cell lysis using an electrochemical method.

The present inventors conducted research on a method of lysing a cell or a virus, based on the prior technologies, and discovered that by using an electrochemical method which is a combination of an electrical method with a chemical method, both of which are known in the art, an amount of free radicals produced increases and thus, the cells can be efficiently lysed.

SUMMARY OF THE INVENTION

The present invention provides a method of lysing a cell using a free radical, which has high cell lysis efficiency and can be easily applied to a microsystem during cell lysis and requires a low electrical power, thus being suitable to realize a lab-on-a-chip (LOC).

According to an aspect of the present invention, there is provided a method of lysing a cell or a virus using a free radical, comprising: applying an electric field to a mixture of a metal ion, a peroxide, and a cell or virus solution to increase the free radical generation, thereby lysing a cell or a virus.

A source of the metal ion may be selected from the group consisting of a metal ion powder, a metal electrode, and a metal bead.

The metal ion may be selected from the group consisting of $Fe^{2+}$, $Cu^{2+}$, $Mn^{2+}$, $Cr^{2+}$, and $Ti^{2+}$.

The peroxide may be hydrogen peroxide or a mixture of hydrogen peroxide with an acid.

The metal ion may be derived from $Fe_2(SO_4)_3 \cdot xH_2O$ and the peroxide may be hydrogen peroxide.

The generated free radical may be selected from the group consisting of a hydroxyl radical, a superoxide radical, and singlet oxygen ($^1O_2$).

The mixture may be obtained in a Y-shaped microchannel which has a first microchannel and a second microchannel merging into one channel, by transporting the metal ion and the peroxde through the first microchannel and the cell or virus solution through the second microchannel, thereby joining the metal ion and peroxde, and the cell or virus solution together.

The electric field may be generated by electrodes installed in a microchannel of a mirofluidic apparatus.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Hereinafter, the present invention will be described in more detail.

According to an embodiment of the present invention, there is provided a method of lysing a cell or a virus using a free radical, comprising: applying an electric field to a mixture of a metal ion, a peroxide, and a cell or virus solution to increase the free radical generation, thereby lysing a cell or a virus.

In the present embodiment, the cell is lysed using the free radical generated using the metal ion and the peroxide, which is an oxidant. Particularly, an electric field is applied to the mixture of the metal ion, the peroxide, and the cell or virus solution to induce a catalytic reaction of the mixture, thereby increasing an amount of the free radical produced, and thus cell lysis efficiency.

A reactive oxygen is an oxygen atom or molecule having an unpaired electron, formed during energy generation. Since the reactive oxygen is very unstable, it binds other surrounding substances to destroy a cell membrane, mitochondria, DNA, and other cell components. As a result, tissues and organs of organisms are damaged, and thus, natural defense mechanisms of the organisms are deteriorated.

A free radical refer to an atom group having an unpaired electron. Generally, a molecule has a pair of electrons which have spin directions opposite to each other, and thus, is present in a stable state. However, the free radical has an unpaired, active electron, and thus, generally unstable and very reactive and has a short lifetime. Since the unpaired electron does not participate in formation of a covalent bond, a center atom has less chemical bonds than the number of valence.

Examples of an oxygen radical include superoxide anion ($O^{2-}$), hydrogen peroxide ($H_2O_2$), a hydroxyl radical (.OH), nitrogen monoxide (NO), and singlet oxygen ($^1O_2$).

A hydroxyl radical is generated by the Fenton reaction, in which $H_2O_2$ and redox-reactive transition metal (Fe(II) or Cu(I)) participate, as follows:

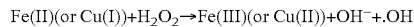

Fe(II)(or Cu(I))+$H_2O_2$→Fe(III)(or Cu(II))+$OH^-$+.OH

A hydroxyl radical is the most reactive among the reactive oxygen species (rate coefficient: generally, $10^9 \sim 10^{11} M^{-1} s^{-1}$) and has a short lifetime (half life: $10^{-10}$ seconds), and thus, cannot reach a concentration sufficient to be analyzed in itself.

Figure 1:
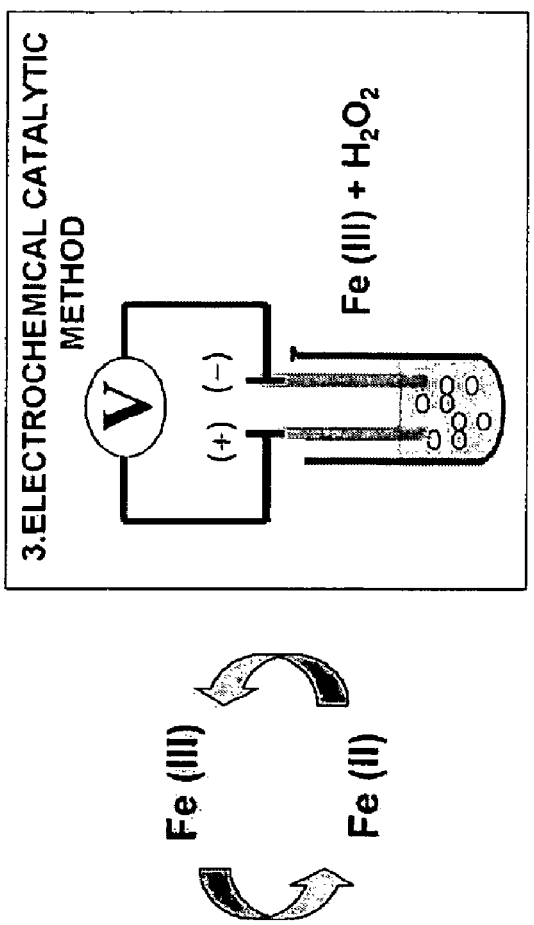
FIG. 1 is a schematic view illustrating three methods comprising generating a hydroxyl radical.
Figure 1:
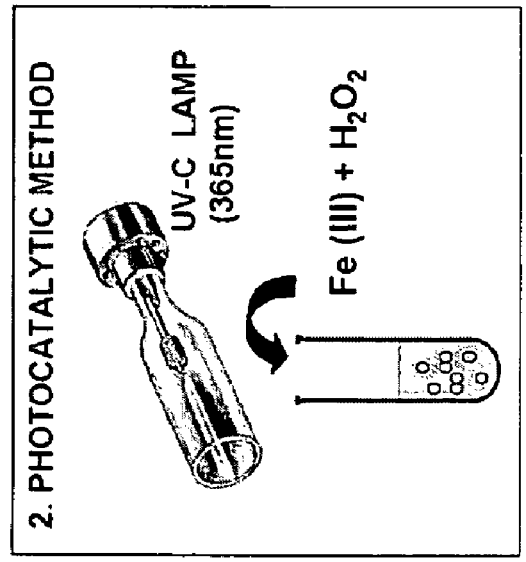
Figure 1:
Figure 1:
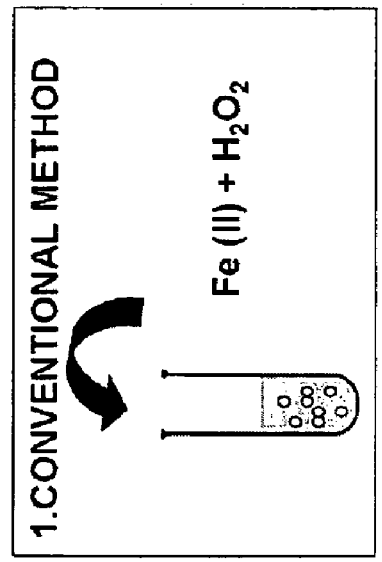

FIG. 1 is a schematic view illustrating three methods comprising generating a hydroxyl radical. In a conventional method, when a metal ion is mixed with hydrogen peroxide, a hydroxyl radical is generated by the Fenton reaction. However, in this method, Fe(III) precipitates and is not reduced to Fe(II). Since the generated free radical is rapidly decomposed, its concentration in the solution is rapidly lowered, thus resulting in low cell lysis efficiency. Thus, to generate a large amount of hydroxyl radical, a large amount of Fe(II) should be added to the reaction system.

However, when an electric field is applied to the mixture according to the electrochemical catalytic method, the precipitated Fe(III) is reduced to Fe(II) on the anode electrode and the Fenton reaction restarts, thereby increasing an amount of the free radical produced. Thus, a large amount of free radical can be generated even in the presence of a small amount of substrate.

Another method of increasing an amount of a hydroxyl radical produced is a photocatalytic method. In this method, when the above mixture is exposed to UV light using a UV light lamp, reduction of Fe(III) to Fe(II) occurs on the cathode electrode, thereby increasing the amount of the free radical produced.

When a cell or virus solution is mixed with the free radical generated using the above method, the free radical attracts an electron from the cell or virus to stabilize its valence electron arrangement, thereby lysing the cell or virus.

In an embodiment of the present invention, a source of the metal ion may be selected from the group consisting of a metal ion powder, a metal electrode, and a metal bead. The source of the metal ion may be any material which contains metal, for example, a compound such as $Fe_2(SO_4)_3 \cdot xH_2O$, a metal ion powder containing metal, a metal electrode, a metal bead.

In an embodiment of the present invention, the metal ion may be selected from the group consisting of $Fe^{2+}$, $Cu^{2+}$, $Mn^{2+}$, $Cr^{2+}$, and $Ti^{2+}$. The metal ion may be any transition metal which has a redox activity.

In an embodiment of the present invention, the peroxide may be hydrogen peroxide or a mixture of hydrogen peroxide with an acid. The acid may be hydrochloric acid, or nitric acid, etc. The peroxide refers to an oxide having a $O^{2-}$ group in the molecule.

In an embodiment of the present invention, the generated free radical may be selected from the group consisting of a hydroxyl radical, a superoxide radical, and singlet oxygen ($^1O^2$).

In an embodiment of the present invention, the mixture may be obtained in a Y-shaped microchannel which has a first microchannel and a second microchannel merging into one, by transporting the metal ion and the peroxde through the first microchannel and the cell or virus solution through the second microchannel, thereby joining the metal ion and peroxde, and the cell or virus solution together. Alternatively, the metal ion and peroxide may be previously mixed with the cell or virus solution. In the Y-shaped microchannel, the metal ion and peroxide is injected into the first microchannel and the cell or virus solution is injected into the second microchannel, and then, cell lysis can occur at a location where the first and second microchannels merge into one. Thus, cell lysis may be performed at a desired time and in a desired space when the present method is applied to a microsystem.

In an embodiment of the present invention, the electric field may be generated by electrodes installed in a microchannel of a mirofluidic apparatus. When the electric field is applied to the mixture using the electrodes which are present in a specific location of the microchannel, the cell or virus injected into the microchannel can be lysed at the location of the electrode where the amount of the radical produced is increased. Thus, cell lysis can be performed only in a desired space.

Hereinafter, the present invention will be described in more detail with reference to the following examples. However, these examples are given for the purpose of illustration and are not intended to limit the scope of the invention.

PREPARATION EXAMPLE 1

Bacteria, Primers, and Polymerase Chain Reaction (PCR)

Plasmid was recombined with human hepatitis B virus (HBV) gene and *E. coli* strains DH5 α (3 ml) were transformed with the plamid and incubated in LB medium (Sambrook et al, 1989) at 37° C. in an aerobic condition until a logarithm phase ($OD_{600}$=0.64). The bacterium cells were collected by centrifuge and washed twice with 3 ml of phosphate buffered saline (PBS). The cells were resuspended in PBS (cell density; $1 \times 10^8$ cells/ml)

To detect DNAs released from the lysed cells, the following PCR primers were used: primer TMP5-F (SEQ ID No. 1) and primer TMP5-R (SEQ ID No. 2). The pair of primers corresponds to a core region of HBV genome. PCR amplification was carried out using Taq polymerase (Takara, Korea) as follows: pre-denaturation at 50° C. for 10 minutes and 95° C. for 1 minute and 50 cycles with each cycle including denaturation at 95° C. for 5 sec and annealing and extension at 62° C. for 15 sec. The obtained amplified PCR products were analyzed using Agilent BioAnalyzer 2100 (Agilent Technologies, Palo Alto, Calif.) together with a DNA 500 assay kit.

PREPARATION EXAMPLE 2

Measurement of Cell Survival

The number of surviving cells was measured based on a colony-forming ability of a single cell. A stock solution of recombinant E. coli (ATCC #45020) or a stock solution of bacterium was aliquoted in LB (10 g/l tryptone, 5 g/l yeast extract, 15 g/l agar, and 10 g/l NaCl) agar plate containing 50 mg/l ampicillin. After incubation at 37° C. for 12 hours, colonies were washed out from a surface of the agar plate and transferred to 10 ml LB medium containing 50 mg/l ampicillin. 1 ml of the cells were placed into a 100 ml shaking flask and incubated at 37° C. and 250 rpm for 6-8 hours. Shaking flask culture of E. coli cells were performed. The cells were washed with 1 × PBS purchased from Gibco (NY, USA) and resuspended, and then centrifuged using Eppendorf 5810R centrifuge (Eppendorf AG, Hamburg, Germany) at 6,000 g and 4° C. for 10 minutes.

After cell lysis was performed using free radicals, the resultant solution was centrifuged at 13,200 rpm for 5 minutes. The supernatant was removed and remaining precipitates were resuspended with 1×PBS. The resultant solution was aliquoted in an agar plate and incubated at 37° C. for 12 hours, and then colonies were observed.

COMPARATIVE EXAMPLE 1

Effects of hydroxyl Radicals Generated by the Conventional Fenton Reaction on Cell Survival and PCR Amplification Effects of hydroxyl radicals generated by the conventional Fenton reaction on cell survival and PCR amplification were evaluated using E. coli strains transformed with plasmid which was recombined with HBV gene.

Figure 2A:
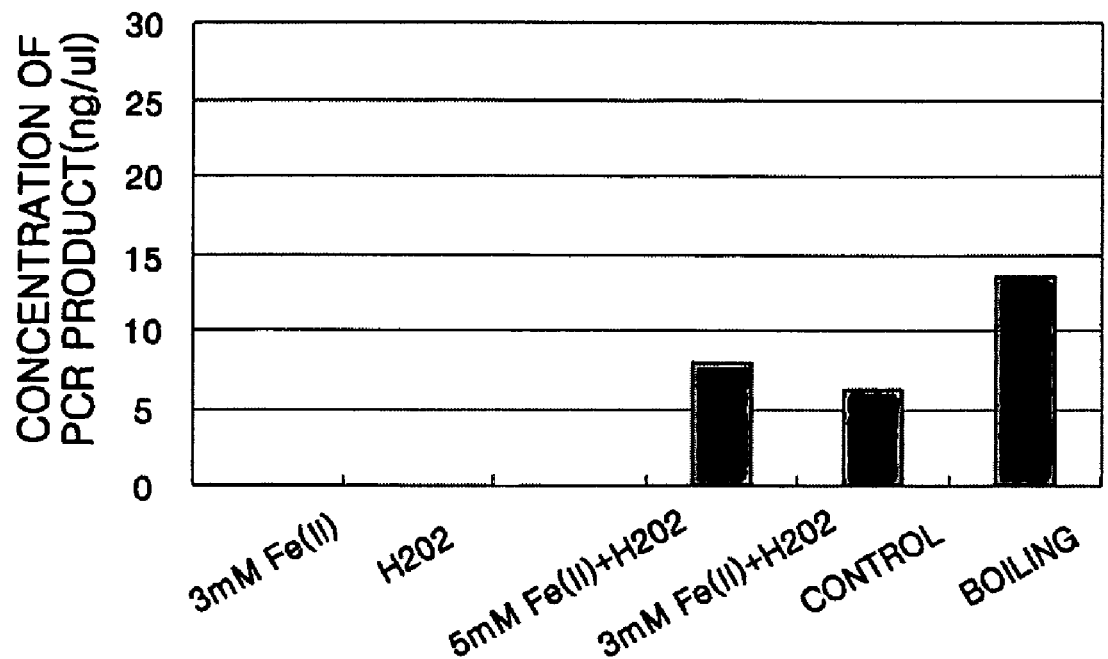
FIG. 2A is a graph showing polymerase chain reaction (PCR) amplification of DNA released by cell lysis using hydroxyl radicals generated by the conventional Fenton reaction.

FIG. 2A is a graph showing PCR amplification of DNA released by cell lysis using hydroxyl radicals which are generated by the conventional Fenton reaction. In this experiment, 3 mM and 5 mM $FeSO_4.7H_2O$ as a source of Fe(II) and 30% $H_2O_2$ were used. The cell culture was centrifuged to obtain a supernatant, which was used a control. In a boiling method, the cell culture was treated at 95° C. for 5 minutes. The cell lysis reaction was performed in PBS buffer, pH 7.4 in a tube for 30 minutes. As a result of PCR amplification of DNA released by cell lysis using hydroxyl radicals generated by the Fenton reaction, when cell lysis was performed using Fe(II) and/or $H_2O_2$, concentrations of PCR products were lower than a concentration of a PCR product when cell lysis was performed using the boiling method. It was confirmed that hydroxyl radical cannot be efficiently generated in the above conditions and a high concentration of Fe(II) can inhibit PCR.

Figure 2B:
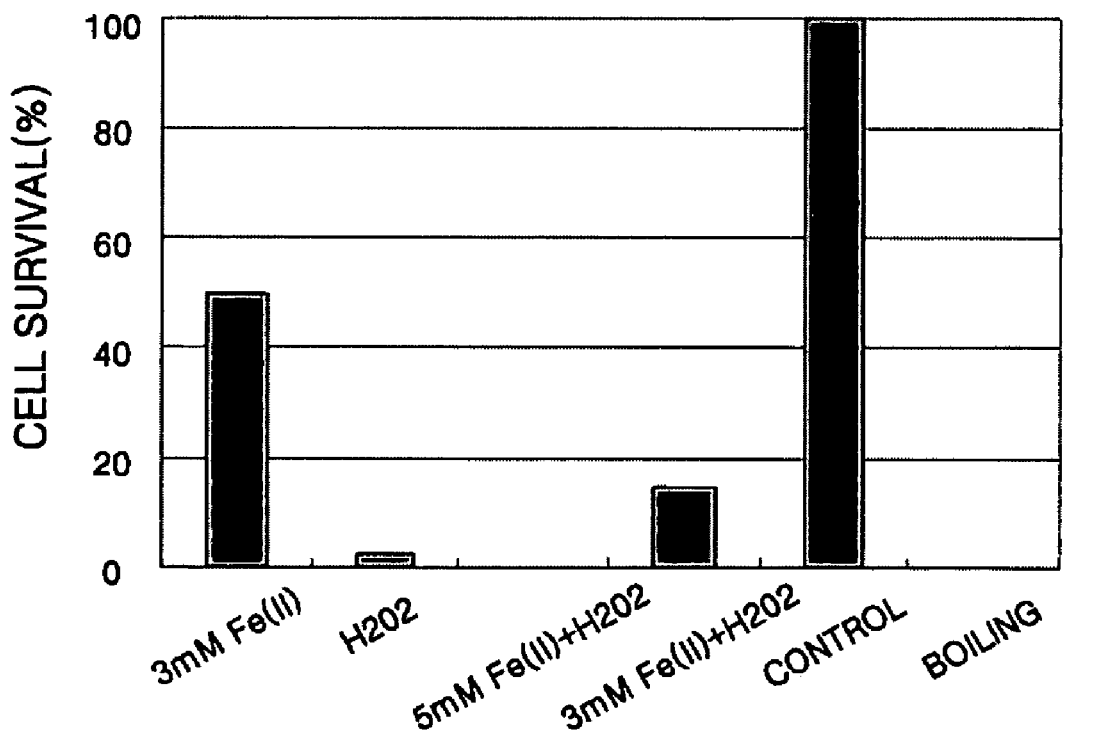
FIG. 2B is a graph showing survival of cells subjected to the cell lysis.

FIG. 2B is a graph showing survival of cell subjected the above-mentioned cell lysis using hydroxyl radicals generated by the Fenton reaction. After cell lysis was performed in the same manner as described above, cell survival was determined. When $H_2O_2$ was used, little cell survived and when the boiling method was used, none of the cell survived. It appears as if these results did not match the results shown in FIG. 2A since when the cell survival is low, production of the PCR products must be high due to a large amount of lysed cells. In this experiment, however, a small amount of PCR products were produced with low cell survival. This is the reason why a high concentration of $H_2O_2$ lowers the cell survival. $H_2O_2$ does not lyse the cells, but inactivates the cells, thereby decreasing the cell survival. Thus, a small amount of PCR products were obtained even Without the cells being lysed.

COMPARATIVE EXAMPLE 2

Effects of Hydroxyl Radicals Generated by a Photocatalytic Method on PCR Amplification Effects of hydroxyl radicals generated by a photocatalytic method on PCR amplification were evaluated using E. coli strains transformed with plasmid which was recombined with HBV gene.

Figure 3:
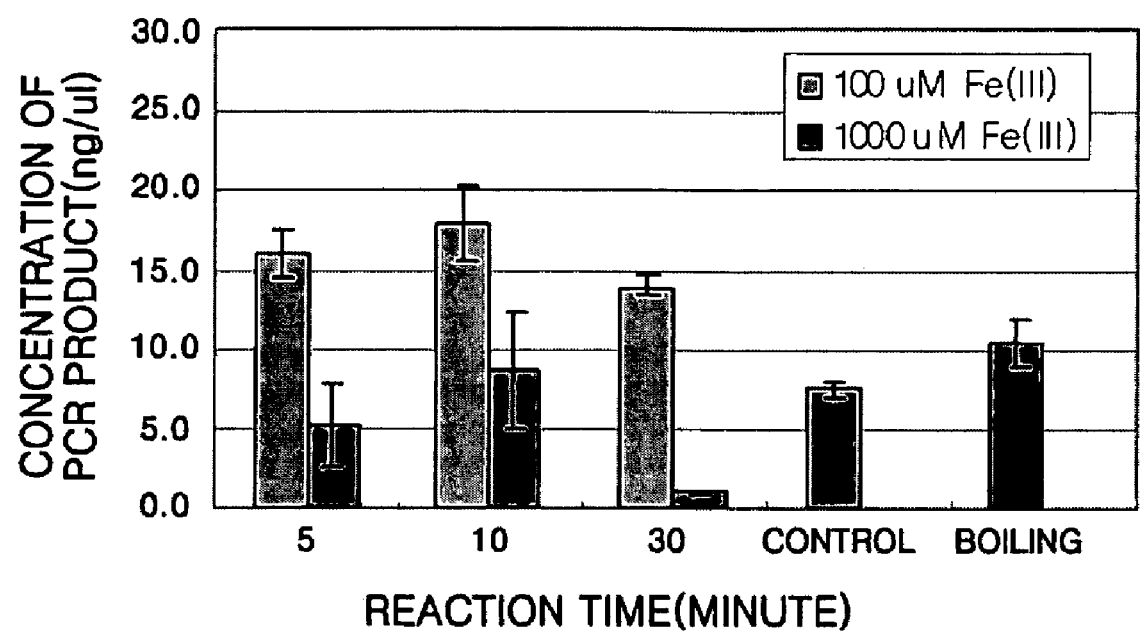
FIG. 3 is a graph showing PCR amplification of DNA released by cell lysis using hydroxyl radicals generated by a photocatalytic method.

FIG. 3 is a graph showing PCR amplification of DNA released by cell lysis using hydroxyl radicals generated by a photocatalytic method. In this experiment, 100 µM and 1000 µM $Fe_2(SO_4)_3.xH_2O$ as a source of Fe(III) and 30% $H_2O_2$ were used. The cell culture was exposed to UV light for 30 minutes using a UV lamp and centrifuged to obtain a supernatant, which was used a control. In a boiling method, the cell culture was treated at 95° C. for 5 minutes. The cell lysis reaction was performed in PBS buffer, pH 7.4 in a tube for 5, 10, and 30 minutes, respectively. The UV light had a main peak of 365 nm and UV power of about 2 W. Referring to FIG. 3, when using 100 µM Fe(III), concentrations of PCR products were higher than a concentration of a PCR product when using the boiling method. Meanwhile, when using 1000 µM Fe(III), concentrations of PCR products were lower than a concentration of a PCR product when using the boiling method. That is, 1000 µM Fe(III) greatly inhibited the PCR amplification and did not aid to increase the cell lysis efficiency. These results show that a probability that the cells are lysed due to UV irridation in addition to the hydroxyl radical cannot be completely excluded. The cell survivals were determined as 0 %, which demonstrates that all the cells were inactivated due to UV irradiation (the data is not shown).

Thus, it is regarded that the method used in Comparative Example 2 still has many problems to overcome for use as a cell lysis method using hydroxyl radical.

EXAMPLE 1

Effects of Hydroxyl Radicals Generated by an Electrochemical Catalytic Method on PCR Amplification Effects of hydroxyl radicals generated by an electrochemical catalytic method according to an embodiment of the present invention on PCR amplification were evaluated using E. coli strains transformed with plasmid which was recombined with HBV gene.

Figure 4:
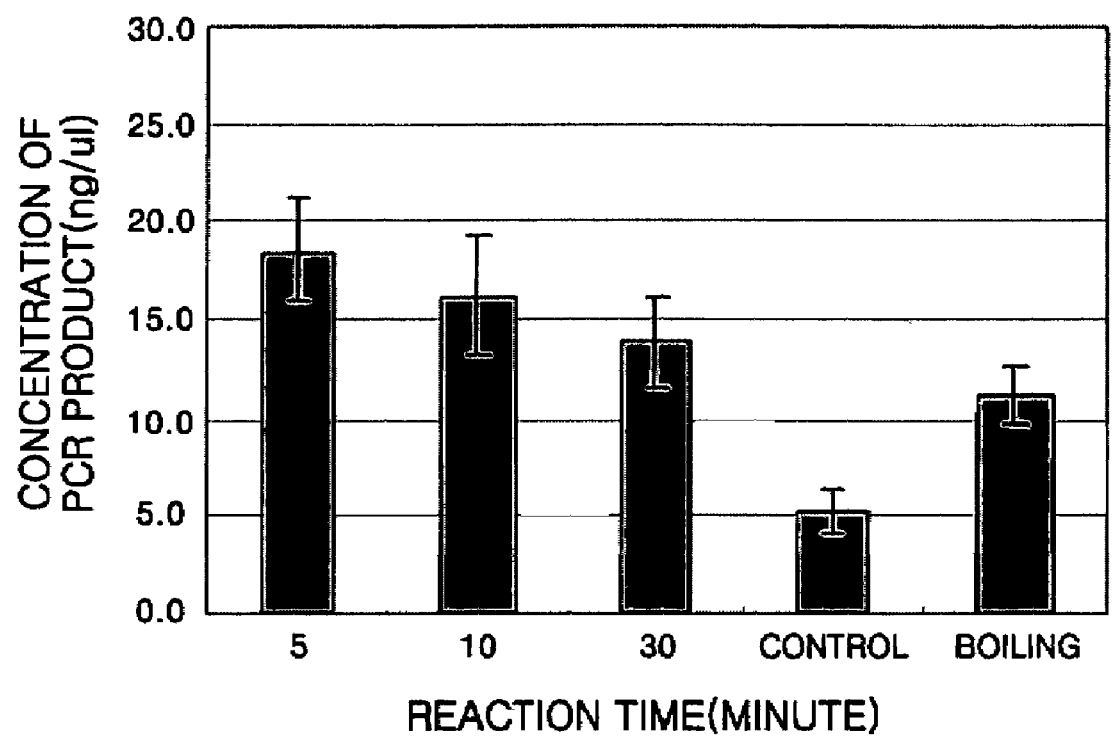
FIG. 4 is a graph showing PCR amplification of DNA released by cell lysis using hydroxyl radicals generated by an electrochemical catalytic method according to an embodiment of the present invention.

FIG. 4 is a graph showing PCR amplification of DNA released by cell lysis using hydroxyl radicals generated by an electrochemical catalytic method according to an embodiment of the present invention. In this experiment, 100 µM $Fe_2(SO_4)_3 \cdot xH_2O$ as a source of Fe(III) and 30% $H_2O_2$ were used. The cell culture was left for 30 minutes in an electrical field and centrifuged to obtain a supernatant, which was used a control. In a boiling method, the cell culture was treated at 95° C. for 5 minutes. The cell lysis reaction was performed in PBS buffer, pH 7.4 in a tube for 5, 10, and 30 minutes, respectively. Conditions of an electric field were as follows: 1 mM NaCl was used as an electrolyte, voltage was 1.5V, and a gold electrode (radius, 2 mm) was used. Referring to FIG. 4, when using 100 µM Fe(III), concentrations of PCR products were higher than a concentration of a PCR product when using the boiling method. That is, when the electrochemical catalytic method according to an embodiment of the present invention was used to lyse the cells, the cell lysis efficiency was higher than when using the boiling method. Meanwhile, it was confirmed that as the reaction time increases, the concentration of PCR products decreases. It is assumed that the cells or released DNAs are adsorbed on the electrode, thereby decreasing the concentration of PCR products.

Thus, a method of lysing a cell using a free radical generated using an electrochemical catalytic method according to an embodiment of the present invention, has higher cell lysis efficiency than the conventional boiling method and can be easily applied to a microsystem. Thus, the method can be used as a cell lysis method which is suitable to realize an LOC.

As described above, in the method according to the present invention, cell lysis may be efficiently performed using a low electrical energy (several mV to several V). When the method according to the present invention is applied to a microsystem, cell lysis can occur at a desired time and in a desired space by controlling the electrical energy, thus the method being suitable to realize an LOC.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method of lysing a cell or a virus using a free radical, comprising:
   applying an electric field to a mixture of a metal ion, hydrogen peroxide, and a cell or virus solution to increase free radical generation in the absence of an acid, thereby lysing a cell or a virus.

2. The method of claim 1, wherein a source of the metal ion is selected from the group consisting of a metal ion powder, a metal electrode, and a metal bead.

3. The method of claim 1, wherein the metal ion is selected from the group consisting of $Fe^{2+}$, $Cu^{2+}$, $Mn^{2+}$, $Cr^{2+}$, and $Ti^{2+}$.

4. The method of claim 1, wherein the metal ion is derived from $Fe_2(SO_4)_3 \cdot xH_2O$.

5. The method of claim 4, wherein the concentration of $Fe_2(SO_4)_3 \cdot xH_2O$ is 100 µM.

6. The method of claim 4, wherein the concentration of $Fe_2(SO_4)_3 \cdot xH_2O$ is 100 µM, the concentration of the hydrogen peroxide is 30%, and the electric field is applied at 1.5 V.

7. The method of claim 6, further comprising amplifying nucleic acid released from the lysed cell or virus in a polymerase chain reaction.

8. The method of claim 1, wherein the generated free radical is selected from the group consisting of a hydroxyl radical, a superoxide radical, and singlet oxygen ($^1O_2$).

9. The method of claim 1, wherein the mixture is obtained in a Y-shaped microchannel which has a first microchannel and a second microchannel merging into one channel, by transporting the metal ion and hydrogen peroxide through the first microchannel and the cell or virus solution through the second microchannel, thereby joining the metal ion and hydrogen peroxide, and the cell or virus solution together.

SEQUENCE LISTING

<160> NUMBER OF SEQ ID NOS: 2

<210> SEQ ID NO 1
<211> LENGTH: 19
<212> TYPE: DNA
<213> ORGANISM: Artificial
<220> FEATURE:
<223> OTHER INFORMATION: forward primer

<400> SEQUENCE: 1
agtgtggatt cgcactcct                                                19

<210> SEQ ID NO 2
<211> LENGTH: 23
<212> TYPE: DNA
<213> ORGANISM: Artificial
<220> FEATURE:
<223> OTHER INFORMATION: reverse primer

<400> SEQUENCE: 2
gagttcttct tctaggggac ctg                                           23

10. The method of claim 1, wherein the electric field is generated by electrodes installed in a micro channel of a mirofluidic apparatus.

11. The method of claim 1, wherein the concentration of the hydrogen peroxide is 30%.

12. The method of claim 1, further comprising amplifying nucleic acid released from the lysed cell or virus in a polymerase chain reaction (PCR).

13. The method of claim 1, wherein the electric field is applied at 1.5 V.

\* \* \* \* \*